United States Patent [19]

Kojima et al.

[11] Patent Number: 4,537,997
[45] Date of Patent: Aug. 27, 1985

[54] PROCESS FOR TREATING HYDROFORMYLATION CATALYST

[75] Inventors: Hidetaka Kojima; Takeshi Horikawa; Masahiro Kagotani, all of Himeji, Japan

[73] Assignees: Daicel Chemical Industries, Ltd., Sakai; Kuraray Co., Ltd., Kurashiki, both of Japan

[21] Appl. No.: 557,763

[22] Filed: Dec. 2, 1983

[30] Foreign Application Priority Data

Dec. 15, 1982 [JP] Japan .................................. 57-219650

[51] Int. Cl.³ .............................................. C07C 45/50
[52] U.S. Cl. ........................................ 568/454; 502/34
[58] Field of Search ........................ 568/454, 882, 909; 502/34, 53

[56] References Cited

U.S. PATENT DOCUMENTS

| | | | |
|---|---|---|---|
| 3,527,809 | 9/1970 | Pruett | 568/454 |
| 3,917,661 | 11/1975 | Pruett | 260/410.9 |
| 4,108,905 | 8/1978 | Wilkinson | 568/454 |
| 4,151,209 | 4/1979 | Paul et al. | 568/454 |
| 4,196,096 | 4/1980 | Dawes et al. | 502/38 |
| 4,215,077 | 7/1980 | Matsumoto et al. | 568/454 |
| 4,297,239 | 10/1981 | Bryant et al. | 568/454 |

FOREIGN PATENT DOCUMENTS 2075857  11/1981  United Kingdom ................ 568/454

Primary Examiner—Werren B. Lone
Attorney, Agent, or Firm—Flynn, Thiel, Boutell & Tanis

[57] ABSTRACT

In a process for producing an aldehyde by hydroformylating allyl alcohol with carbon monoxide and hydrogen gas in the presence of a catalyst comprising a rhodium compound and a tertiary phosphine in an organic solvent and separating the resulting aldehyde with water extraction from the reaction mixture, the catalyst is maintained and recovered in the activity by treating the catalyst-containing solution in the organic solvent with a gaseous mixture of carbon monoxide and hydrogen gas after the water extraction step.

8 Claims, No Drawings

PROCESS FOR TREATING HYDROFORMYLATION CATALYST

This invention relates to a process for treatment of a rhodium-containing hydroformylation catalyst to keep the high activity of the catalyst. In particular the invention applies effectively to the catalyst which has been used for the hydroformylation process of allyl alcohol so that the catalyst may be recovered and maintained in respect to the activity thereof.

It is known that allyl alcohol is hydroformylated in the presence of a catalyst comprising a rhodium compound and a tertiary phosphine and hydroxybutyl aldehyde or the like is obtained, followed by further production of butanediols therefrom. British Pat. No. 14 93 154 discloses that hydroformylation of allyl alcohol is effected in an organic solvent; the obtained aldehyde is extracted with water from the reaction mixture; separately the catalyst-containing solution in the organic solvent is recycled to the reaction system for hydroformulation; and hydrogenation of the aldehyde is carried out in the aqueous phase to obtain a butanediol. According to the process, there is a disadvantage that the activity of the catalyst which has been repeatedly used decreases. In order to solve the problem, U.S. Pat. No. 4,215,077 teaches that the activity of the catalyst can be maintained by adding a phosphine compound to the reaction system.

Apart from the limited field of allyl alcohol, it is, in general, known that the activity of a hydroformylation catalyst for an olefinic compound often decreases with time. In this connection, Japanese patent publication No. 43799/1973 teaches that a rhodium complex catalyst can be activated and recovered by heating with hydrogen gas at an elevated pressure. In examples of the publication, the activity of the catalyst concerned is expressed in terms of a yield of butyraldehyde. The inventors have calculated rate constants of hydroformylation, $K$, based on data of the examples of the publication. They have further determined specific activities, $K/K_0$, in which $K_0$ is an initial value of $K$, in order to study the activity-recovering effect. According to their study, the catalytic activity which had been reduced to 36% was restored to 53% by the treatment with hydrogen under a pressure of 70 kg/cm$^2$ at 60° C. for 14 h. However, the complete recovery to the initial activity could not be attained.

It is described also in U.S. Pat. No. 4,196,096 that various processes were attempted for the regeneration of rhodium catalysts used for the hydroformylation of unsaturated compounds such as $\alpha$-olefins. It is also described therein that these numerous processes including a treatment of the deactivated catalyst with a synthesis gas (combination of carbon monoxide and hydrogen used for oxo reactions) were unsatisfactory for the regeneration of the catalyst.

The invention provides an improvement of the catalyst which is used repeatedly in the process where an intended aldehyde is separated with water extraction from the reaction mixture of hydroformylation of allyl alcohol. The invention has a primary purpose that the activity of the rhodium-phosphine catalyst for the reaction is maintained and a decreased activity is ameliorated so that the catalyst can be used for a long period of time. The invention provides a method for treating the catalyst for the purpose. In a process for producing an aldehyde by hydroformylating allyl alcohol with carbon monoxide and hydrogen gas in the presence of a catalyst comprising a rhodium compound and a tertiary phosphine in an organic solvent and separating the resulting aldehyde with water extraction from the reaction mixture, the invention provides the improvement which comprises treating the catalyst-containing solution in the organic solvent with a gaseous mixture of carbon monoxide and hydrogen gas at a volume ratio of 1:99 to 80:20 at a temperature of 40° to 100° C. after the water extraction step in order to maintain and restore the activity of the catalyst.

It has been known that rhodium/phosphine catalysts have a high activity capable of carrying out the hydroformylation reaction under mild reaction conditions. Under these characteristically mild conditions, substances which poison the hydroformylation catalyst cannot be decomposed. Accordingly, if the catalyst is used for a long time, it is poisoned by minor constituents contained in the starting gas and liquor, such as oxygen, halogens or sulfur, oxidation by-products such as organic acids, and aldehyde condensates and, therefore, the activity thereof is reduced seriously or it is substantially deactivated. In particular, during the hydroformylation of allyl alcohol, the serious activity reduction was recognized as shown in the Referential Example given below.

The deterioration of the catalytic activity in the rhodium-catalyzed hydroformylation is often observed. For example, a close relationship between the activity and color of a rhodium catalyst used for the hydroformylation of unsaturated compounds such as $\alpha$-olefins is disclosed in the specification of Japanese Patent Laid-Open No. 106545/1980. It is described therein that rhodium complex catalysts having a sufficient activity are wheat straw-colored, while deactivated catalysts are black. On the contrary, in the hydroformylation of allyl alcohol, the catalytic activity is sometimes deteriorated even if the yellow, transparent appearance of the catalyst solution is maintained.

The hydroformylation of allyl alcohol is an important step in the process for obtaining butanediols. In addition, the rhodium complex to be used for the catalyst is very expensive material. Therefore, it is disadvantageous that the catalyst is deactivated within such a short time. The development of a simple process for maintaining the catalytic activity or regenerating the deactivated catalyst has eagerly been demanded.

After investigations of causes of the deactivation and counterplans, the inventors supposed that allyl alcohol forms an impurity which is coordinated quite firmly with the rhodium complex via one of the hydroformylation products. One of the typical impurities is methacrolein which is formed as shown below:

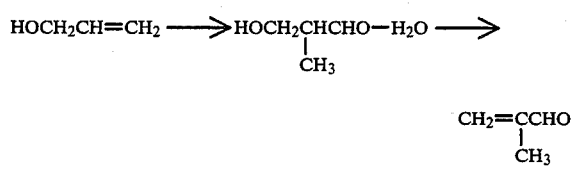

Therefore, the deactivation mechanism is utterly different from that in the hydroformylation of ordinary olefin compounds.

After intensive investigations of the prevention of the reduction in the activity of the rhodium complex catalysts and the maintenance of the high activity by recovering the same, made on the basis of the above finding, the inventors have found that the activity can be recovered under mild conditions by treating the rhodium/tert-phosphine hydroformylation catalyst (hereinafter referred to as rhodium complex catalyst) solution with a gaseous mixture of carbon monoxide and hydrogen in such a state that the catalyst solution is separated from the reaction mixture or, in other words, that neither the starting allyl alcohol nor a major part of the hydroformylation reaction product is present. The present invention has been completed on the basis of this finding.

According to the process of the present invention wherein the catalyst is treated with the gaseous mixture of carbon monoxide and hydrogen, the recovery of an activity to an extent higher than that attained by the treatment with hydrogen alone is possible and the effect can be obtained by the treatment carried out under a quite low pressure for a short time as shown in examples given below.

According to U.S. Pat. No. 4,196,096, the treatment of the inactivated catalyst by a synthesized gas does not result in any satisfaction. Apparently, it seems that the fact described therein is contrary to the effects of the present invention. However, in view of the fact that the mechanisms of the deactivation of the catalyst in the prior technique is utterly different from that of the present invention, it will be understood that said description relating to the prior process is neither contradictory to the present invention nor it does anticipate the present invention.

Further, it has been known that the presence of carbon monoxide exhibits generally an adverse effect on the hydrogenation reaction velocity of olefinic compounds. A gaseous mixture of carbon monoxide and hydrogen has been used for the hydroformylation reaction itself and in contact with the catalyst throughout the reaction. Thus it has not been expected that if the catalyst is treated again with a gaseous mixture of carbon monoxide and hydrogen after separating the same from the reaction mixture, an effect of recovering the activity superior to that obtained by using hydrogen alone can be obtained.

It is an important problem to maintain the activity of the hydroformylation catalyst for a long time. There have been proposed some ideas of recovering the catalytic activity by methods other than the treatment of the catalyst solution. These ideas include purification of the starting materials or maintenance and separation of the catalyst solution.

Though those methods make the life of the catalyst rather longer, a reaction rate is decreased down to a value which would not be practically used.

The deactivated catalyst solution is sent to a catalyst manufacturer to recover rhodium [see "Shokubai (Catalysts)" Vol. 23, p. 174]. There has not been proposed a simple and effective process for recovering the activity as in the present invention.

The rhodium complex catalysts treated according to the present invention are those well known in U.S. Pat. Nos. 3,527,809, 3,917,661 and 4,108,905. Any of the rhodium complex catalysts easily convertible into $HRh(CO)(PR_3)_3$ in the presence of CO, $H_2$ and tert-phosphine, e.g., rhodium carbonyl compounds such as $Rh(CO)_2$ (Acetylacetonate), $Rh_4(CO)_{12}$ or $Rh_6(CO)_{16}$, may be used as the catalyst.

The tertiary phosphine to be used according to the invention includes triaryl phosphines such as triphenyl phosphine, tritolyl phosphine and trinaphthyl phosphine; trialkyl phosphines having 1 to 8 carbon atoms in the alkyl, such as butyl and octyl; diarylalkyl phosphines such as diphenylmethyl phosphine; triaralkyl phosphines having aralkyls such as benzyl and phenetyl; and bis(diarylphosphino)alkanes as shown in U.S. Pat. No. 4,215,077, for example having the formula: $(C_6H_5)_2P(CH_2)_nP(C_6H_5)_2$, wherein n represents a number of 1 to 6.

The above listed tertiary phosphines may be used by themselves or in the form of a mixture with each other. Especially the triaryl phosphine or a mixture of the triaryl phosphine and the bis(diarylphosphino) alkane is preferred.

They may contain phosphine oxide which is an oxidation product of the tert phosphines.

In the process of the present invention, the hydroformylation catalyst is treated in the form of the organic solvent solution after the produced aldehydes have been removed out with water extraction. The treatment is effected with a gaseous mixture of carbon monoxide and hydrogen (hereinafter referred to as gaseous $CO/H_2$ mixture).

As the organic solvents, aromatic hydrocarbons such as benzene, toluene, xylene or ethylbenzene are used generally. In addition, aromatic esters such as octyl phthalate and other organic solvents known to be usable in the hydroformylation reaction may also be used.

Now, description will be made on the conditions of the hydroformylation reaction carried out in the presence of the catalyst treated by the process of the present invention. The pressure may be atmospheric or higher pressure. From the viewpoint of productivity and economy, a pressure of about 1 to 30 kg/cm$^2$G is preferred. The reaction temperature is generally 20° to 200° C., preferably 50° to 120° C.

The characteristic treatment with the gaseous $CO/H_2$ mixture according to the present invention is applicable to the catalyst solution containing an ordinary rhodium complex catalyst as described above. The catalyst solution is treated with the gaseous $CO/H_2$ mixture after separating the same from a major part of formed aldehyde and unreacted allyl alcohol contained in the reaction mixture. However, the presence of a very small amount of the aldehyde or the like still remaining after the extraction with water is allowable.

The hydroformylation reaction activity can be recovered by treating the solution of the hydroformylation catalyst having a reduced activity with the gaseous $CO/H_2$ mixture. In addition, if the solution of the hydroformylation catalyst used to some extent but the activity of which has not been reduced significantly is passed through the gaseous $CO/H_2$ mixture treatment zone in the same manner as above, the accumulation of the poisoned catalyst can be prevented and, thereby, the activity reduction can also be prevented.

The gaseous $CO/H_2$ mixture used in the present invention is a gaseous mixture of carbon monoxide and hydrogen having a CO content of 1 to 80%, preferably 5 to 50%, and an $H_2$ content of 20 to 99%, preferably 50 to 95%. This gaseous mixture may contain components which do not exert a harmful influence on the rhodium complex catalyst, such as methane, nitrogen or argon.

The pressure of the treatment with the gaseous $CO/H_2$ mixture is at least 1 kg/cm$^2$, practically 1 to 20 kg/cm$^2$ (abs.), preferably 3 to 20 kg/cm$^2$, more preferably 3 to 10 kg/cm$^2$. A pressure higher than 20 kg/cm$^2$ may also be used but no more additional effect can be obtained by elevating the pressure.

The treatment temperature is practically 40° to 100° C., preferably 50° to 80° C. If an excessively high temperature is employed, the catalyst is easily deteriorated and harmful influences of the aldehyde or the like still remaining in only a very small amount are realized and only a low effect can be obtained or even the activity is reduced unfavorably in some cases by such high temperature treatment. In Example 4 given below, higher than 90% of the initial activity was recovered by the treatment carried out at 90° C. but the recovery of such a high activity could not be obtained when the treatment temperature was elevated to 120° C. The treatment time which varies depending on the degree of activity reduction is generally about 0.5 to 5 hours.

The following examples will further illustrate the present invention. At first, a method of determination of the catalytic activity is shown. The hydroformylation reaction for obtaining a catalyst having a reduced activity to be treated with the gaseous mixture of CO and $H_2$ is shown in the Referential Example.

In the following examples, a toluene solution containing $HRh(CO)(PPh_3)_3$ (0.6-2 mmol/l) and $PPh_3$ (100-200 mmol/l) was used as the rhodium complex catalyst solution.

In measurement of the catalyst activity, 0.1 mol/l of allyl alcohol was added to the rhodium complex catalyst solution. A gaseous $CO/H_2$ mixture (CO content: 50%) was introduced therein under stirring to carry out the hydroformylation reaction at 60° C. under 1 atm. Allyl alcohol consumption rate constant ($h^{-1}$) was determined to evaluate the catalyst activity.

Referential Example

The rhodium complex catalyst solution was mixed with allyl alcohol in such an amount that the allyl alcohol concentration would be 2 mol/l. The mixture was charged continuously in a bubbling column reactor having a liquid capacity of 60 l at the rate of 10 l/h. A gaseous $CO/H_2$ mixture (CO content: 20%) was fed therein to attain the total pressure of 2 kg/cm² and the hydroformylation reaction of allyl alcohol was carried out at 65° C. The reaction product was extracted with water. The rhodium complex catalyst solution was circulated into the reactor. The reaction was continued for 46 hours. After completion of the reaction, the activity was reduced to 1.60 $h^{-1}$, while the initial activity determined by the method shown above was 2.45 $h^{-1}$.

EXAMPLE 1

100 ml of the rhodium complex catalyst solution having the reduced activity shown in Referential Example was charged in a nitrogen-purged 300 ml autoclave provided with a stirrer. A gaseous $CO/H_2$ mixture containing 20% CO was charged therein at 60° C. to elevate the pressure to 10 kg/cm². The mixture was maintained at this temperature under stirring for 2 hours to effect the treatment. After cooling and pressure reduction to atmospheric pressure, the rhodium complex catalyst solution was taken out and the activity thereof was determined by the method shown in measurement of the catalyst activity to reveal that it was recovered to 2.4 $h^{-1}$.

EXAMPLES 2 TO 10

The treatment with the gaseous $CO/H_2$ mixture was effected under the same conditions as in Example 1 except that the CO concentration, total pressure and treatment temperature were varied. The results are shown in Table 1. The results obtained in Example 1 are also shown in Table 1.

TABLE 1

| Example | CO conc. (%) | Total pressure (kg/cm²) | Temperature (°C.) | Activity ($h^{-1}$) |
|---|---|---|---|---|
| 1 | 20 | 10 | 60 | 2.40 |
| 2 | 50 | 10 | 60 | 2.40 |
| 3 | 3 | 10 | 60 | 2.24 |
| 4 | 3 | 10 | 90 | 2.24 |
| 5 | 20 | 10 | 80 | 2.41 |
| 6 | 30 | 10 | 60 | 2.33 |
| 7 | 30 | 10 | 70 | 2.40 |
| 8 | 30 | 10 | 80 | 2.33 |
| 9 | 30 | 4 | 60 | 2.39 |
| 10 | 30 | 7 | 60 | 2.41 |

COMPARATIVE EXAMPLE 1

The treatment was effected under the same conditions as in Example 1 except that the gaseous $CO/H_2$ mixture was replaced with pure CO gas. The activity was 1.10 $h^{-1}$. This fact indicated that the activity was rather reduced.

COMPARATIVE EXAMPLE 2

The treatment was effected under the same conditions as in Example 1 except that the gaseous $CO/H_2$ mixture was replaced with pure hydrogen gas. The activity was 2.1 $h^{-1}$. The recovery was smaller than that obtained by using the gaseous $CO/H_2$ mixture.

The embodiments of the invention in which an exclusive property or privilege is claimed are defined as follows:

1. In a process for producing an aldehyde by hydroformylation of allyl alcohol with carbon monoxide and hydrogen, in the presence of a rhodium-tertiary phosphine complex hydroformylation catalyst, which comprises, in a reaction zone, providing a liquid reaction medium which comprises a solution of said catalyst dissolved in an organic solvent, supplying carbon monoxide, hydrogen and allyl alcohol to said liquid reaction medium under conditions that effect hydroformylation of said allyl alcohol to convert same to the aldehyde, then extracting the aldehyde from the liquid reaction medium with water and separately recovering said solution of said catalyst dissolved in said organic solvent wherein the recovered solution of said catalyst is substantially free of said aldehyde, hydrogen and carbon monoxide and contains spent catalyst, the improvement which comprises: placing said recovered solution in a treatment zone separate from said reaction zone and, in said treatment zone, heating said recovered solution at a temperature of from 40° to 100° C., in contact with a gaseous mixture of carbon monoxide and hydrogen mixed at a volume ratio of from 1:99 to 80:20, to restore the activity of said spent catalyst whereby said solution containing the restored catalyst an be recycled to said reaction zone as said liquid reaction medium.

2. A process as claimed in claim 1, in which the ratio of carbon monoxide to hydrogen gas is in the range of from 5:95 to 50:50.

3. A process as claimed in claim 1, in which the treatment zone is heated at a temperature of 50° to 80° C.

4. A process as claimed in claim 1, in which the pressure of said gaseous mixture in said treatment zone is at least 1 kg/cm².

5. A process as claimed in claim 1, in which the pressure of said gaseous mixture in said treatment zone is from 3 to 20 kg/cm$^2$.

6. A process as claimed in claim 1, in which the catalyst comprises a carbonyl complex of rhodium and triphenyl phosphine.

7. A process as claimed in claim 1, in which the organic solvent is an aromatic hydrocarbon.

8. A process as claimed in claim 1 in which said treatment zone is an autoclave, said recovered solution is charged into said autoclave, then said gaseous mixture is charged into said autoclave to elevate the pressure therein to from 3 to 20 kg/cm$^2$ and the temperature thereof is maintained at from 50° to 80° C. while stirring the contents of the autoclave, for from about 0.5 to about 5.0 hours, in order to restore the activity of said catalyst.

* * * * *